(12) United States Patent
Ziarati et al.

(10) Patent No.: US 10,083,598 B2
(45) Date of Patent: Sep. 25, 2018

(54) ALERT SYSTEM FOR MRI TECHNOLOGIST AND CAREGIVER

(71) Applicant: Resonance Technology, Inc., Northridge, CA (US)

(72) Inventors: Mokhtar Ziarati, North Hollywood, CA (US); Parisa Ziarati, Granada Hills, CA (US)

(73) Assignee: Resonance Technology, Inc., Northridge, CA (US)

( * ) Notice: Subject to any disclaimer, the term of this patent is extended or adjusted under 35 U.S.C. 154(b) by 0 days.

(21) Appl. No.: 15/687,277

(22) Filed: Aug. 25, 2017

(65) Prior Publication Data

US 2018/0144612 A1    May 24, 2018

Related U.S. Application Data

(60) Provisional application No. 62/425,481, filed on Nov. 22, 2016.

(51) Int. Cl.
*A61N 1/08* (2006.01)
*G08B 25/12* (2006.01)
(Continued)

(52) U.S. Cl.
CPC .............. *G08B 25/12* (2013.01); *A61B 5/747* (2013.01); *A61B 5/7465* (2013.01);
(Continued)

(58) Field of Classification Search
CPC ....... A61B 5/746; A61B 5/044; A61B 5/0452; A61B 5/055; A61B 5/0555; A61B 5/14542; A61B 5/742; A61B 5/11; A61B 5/7207; A61B 5/721; A61B 5/7405; A61B 5/7455; A61B 5/7465; A61B 5/747; A61N 1/3718; A61N 1/3925; A61N 1/3956; A61N 1/3962; A61N 1/3987; A61N 1/37252; A61N 1/3931; A61N 1/3704; A61N 1/37217; A61N 1/3993; G01R 33/5673; G01R 33/5676; G06F 19/3418; G16H 10/65;
(Continued)

(56) References Cited

U.S. PATENT DOCUMENTS 5,160,943 A    11/1992 Pettigrew et al.
5,277,184 A    1/1994 Messana
(Continued)

FOREIGN PATENT DOCUMENTS

WO    WO2007134146 A2    11/2007

*Primary Examiner* — Dionne H Pendleton
(74) *Attorney, Agent, or Firm* — Larry K. Roberts

(57) ABSTRACT

An alert system for providing the capability for a care giver or technologist in a medical procedure room such as the magnet room of an MRI installation to send an alert signal to personnel outside the magnet room. The system includes an alert device in the procedure room with an alert switch, and a wireless signal transmitter for generating encoded alert signals upon activation of the alert switch. An alert control system in the control room of the installation includes a signal receiver, a memory for storing pre-recorded messages, an audio transducer and a controller, the controller responsive to alert signals received from the alert device to generate alert signals including generating pre-recorded messages from the audio transducer.

20 Claims, 4 Drawing Sheets

(51) Int. Cl.
| | |
|---|---|
| *A61B 5/00* | (2006.01) |
| *A61N 1/39* | (2006.01) |
| *H04L 29/08* | (2006.01) |
| *H04W 4/80* | (2018.01) |

(52) U.S. Cl.
CPC ............ *A61N 1/3993* (2013.01); *H04L 67/12* (2013.01); *H04W 4/80* (2018.02)

(58) Field of Classification Search
CPC ......... H04L 12/10; H04L 67/12; G08B 25/12; H04W 4/80
See application file for complete search history.

(56) References Cited

U.S. PATENT DOCUMENTS

| | | | |
|---|---|---|---|
| 5,412,419 | A | 5/1995 | Ziarati |
| 5,432,544 | A | 7/1995 | Ziarati |
| 5,627,902 | A | 5/1997 | Ziarati |
| 5,877,732 | A | 3/1999 | Ziarati |
| 5,878,746 | A | 3/1999 | Lemelson |
| 6,215,454 | B1 | 4/2001 | Tran |
| 6,878,112 | B2 | 4/2005 | Linberg et al. |
| 9,454,008 | B2 | 9/2016 | Ziarati |
| 9,571,820 | B2 | 2/2017 | Ziarati |
| 2005/0107681 | A1 | 5/2005 | Griffiths |
| 2012/0109260 | A1* | 5/2012 | Stancer ................ A61N 1/3718 607/60 |
| 2014/0155728 | A1* | 6/2014 | Lee ........................ A61B 6/462 600/407 |
| 2015/0200996 | A1 | 7/2015 | Ziarati |

\* cited by examiner

ALERT SYSTEM FOR MRI TECHNOLOGIST AND CAREGIVER

CROSS-REFERENCE TO RELATED APPLICATION

This application claims the benefit of U.S. Provisional Application No. 62/425,481 filed Nov. 22, 2016, the entire contents of which are hereby incorporated by reference.

BACKGROUND

Imaging technologies such as MRI involve the use of a specially constructed, shielded magnet room and an associated control room. The MRI magnet with the magnet bore is installed in the magnet room, and the control equipment is installed in the control room. The patient is placed onto an MRI platform, which is movable into the MRI bore for the imaging procedure. A technologist or other caregiver typically assist the patient and positions the patient on the equipment for the imaging procedure.

In many occasions during setup with the patient in the MRI or other imaging modality, such as computed tomography (CT), there is an accident and the technologist or caregiver requires help in the MRI room. With the conventional MRI setup, the technologist does not have access to the immediate help from outside the MRI room. This could potentially have negative effect on the safety of the patient and the technologist.

Examples of an "accident" include the patient falling on the technologist, and the technologist simply needing immediate help to position the patient for the procedure, or to assist the patient after the procedure.

BRIEF DESCRIPTION OF THE DRAWINGS

Features and advantages of the disclosure will readily be appreciated by persons skilled in the art from the following detailed description when read in conjunction with the drawing wherein:

FIG. 1A is an isometric diagrammatic view of an IR transmitter/receiver mounted at the window. FIG. 1B is a front view of the IR transmitter/receiver, depicting the sensor. FIGS. 1C, 1D and 1E illustrate an exemplary embodiment of a wearable alert device. FIGS. 1F and 1G illustrate an exemplary embodiment of an alert device mounted to the MRI magnet.

DETAILED DESCRIPTION

Figure 1:
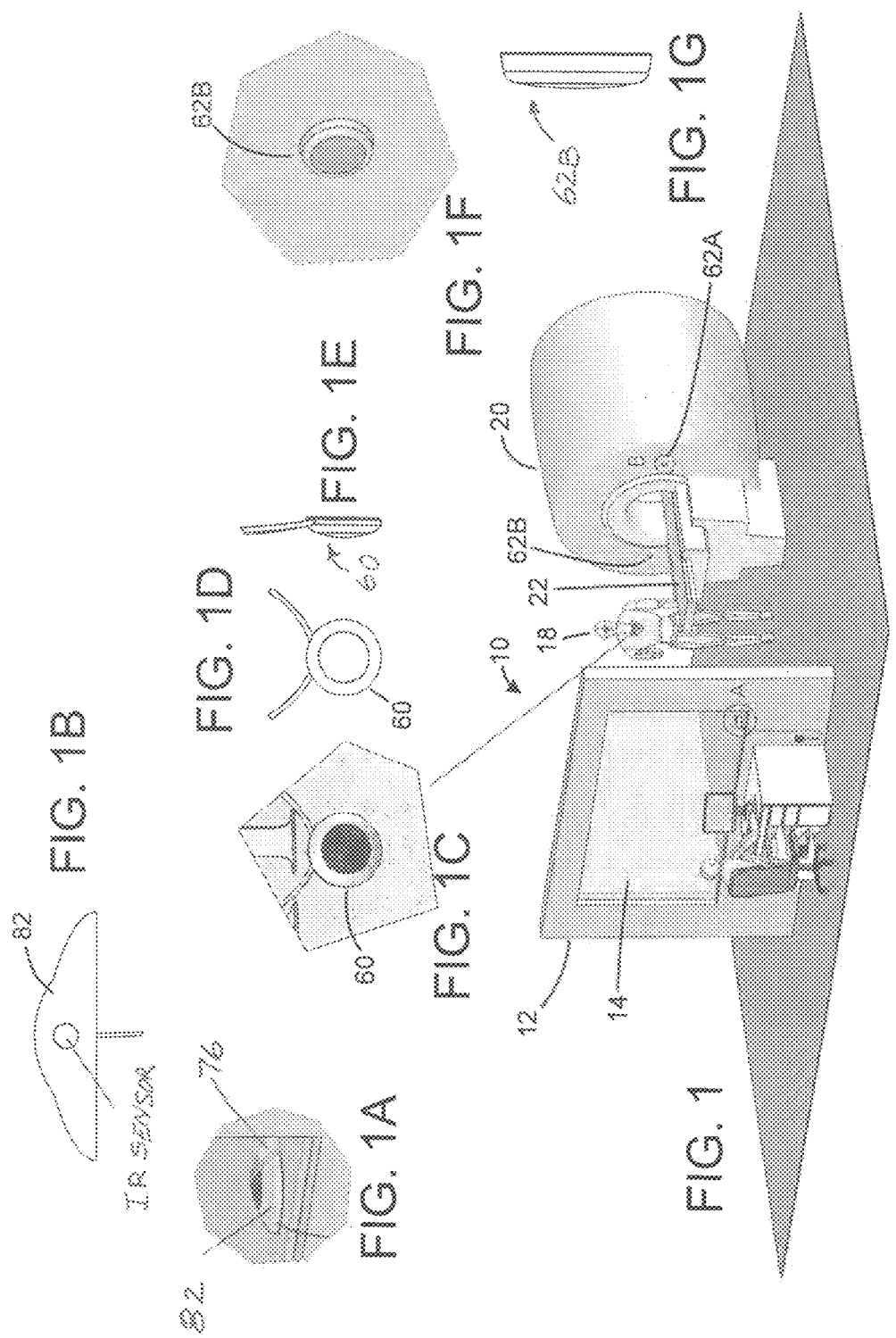
FIG. 1 is a diagrammatic view illustrating an MRI installation, with a magnet room, a control room with separating wall and window, illustrating a technologist or caregiver, and showing features of an alert system.

In the following detailed description and in the several figures of the drawing, like elements are identified with like reference numerals. The figures are not to scale, and relative feature sizes may be exaggerated for illustrative purposes.

In accordance with an aspect of the invention, an alert system is provided, whereby the technologist or other care giver in a medical procedure room such as an MRI magnet room can communicate an alert signal to personnel outside the magnet room, to call attention to the need for assistance in the magnet room. To provide a safe system design for the MRI application, the system is designed so that the radio frequency and the strong magnetic field of the MRI system has no effect on the electronics of the MRI alert system and the alert system does not have any adverse effect on the operation and the image quality of the MRI scanner.

The alert system device could be provided in at least two different types or embodiments. One type is a simple and cost-effective version with no microphone, and only activates an alarm configured to activate a pre-recorded audio alert signal in the control room. A more sophisticated and advanced type has a built-in microphone, and is configured to relay or transmit a voice or audio message to the nurse station, MRI reception area and/or the control room, e.g. in the form of a loud voice.

Ideally every care giver and technologist is provided with a small button-shaped transmitter analogous to a vehicle remote control or fob, with optionally a built-in microphone. The transmitter is designed to be worn on the neck like a necklace, or as a watch-like device to be worn on his or her wrist. The device has an alert button to activate a receiver inside the MRI room. Thus, in effect, the alert signal is transmitted via IR/Wi-Fi/Bluetooth/wire/optical fiber to a central station controller in the control room. As an example, the system can include a base station with an IR transmitter to transmit IR signals through the window between the control room and the MRI room. A receiver at the window or in the control room activates a central station or alert control system located inside the control room, and the received signal is used to activate or to announce the alert via speakers in the control room.

Exemplary features for exemplary embodiments of the system include one or more of the following:

(i) capability to connect, via Wi-Fi/Internet, other alert devices to a selected station or station;

(ii) a simplified version which provides the capability to only activate alert signals such as pre-recorded messages;

(iii) an RF transmitter for the alert device;

(iv) watch and necklace versions of the alert device;

(v) stand-alone version of the alert device to attach to the side of the magnet or other structures in the magnet room;

(vi) the system may have several alert devices active in the same time in the MRI magnet room;

(vii) Bluetooth™ link for direct connection to the control room master receiver and via a network connection to other locations on the network.

FIG. 1 illustrates an exemplary operating environment for an alert system in accordance with an embodiment of the invention. An MRI installation 10 includes a magnet room in which the MRI magnet 20 is disposed. The room walls, floor and ceiling are typically shielded to prevent passage of electromagnetic signals or energy. A control room is separated from the magnet room by a wall 12, in which a window 14 is installed. Typically, the window is shielded to prevent RF energy to pass through it, while allowing light energy, including IR, to pass through. One technologist 18 is illustrated as being within the magnet room adjacent the MRI magnet. The technologist 18 assists and positions the patient to undergo the MRI procedure. The patient is positioned on the platform 22 which moves in and out of the magnet bore.

FIG. 1 diagrammatically discloses the magnet room and the control room, but shows the wall only in partial form for clarity.

To the extent just described. the MRI installation is conventional.

In accordance with aspects of a first embodiment of the invention, the technologist 18 wears a necklace-type alert device 60, which includes a small RF transmitter similar in a general sense to a car remote control. The RF technology has a main advantage of long battery life. It is expected for the battery to last for a year. The alert device is generally non-magnetic.

The battery for the alert device 60 usable in the MRI magnet room is selected to be non-magnetic. MRI-compatible rechargeable batteries with various power and sizes are commercially available. One vendor is at Powerstream.com, for non-magnetic lithium Ion batteries, e.g. model PGEB_NM053040 600 mAht (5×3×4 5 m×30×40 mm). A charger for the battery is Charger PST_LC24. A suitable battery for the receiver is PGEB_NM5858138 (marked NM5858150) (6000 MAN 5.8×58×138 mm). The housing of the alert device is non-magnetic, e.g. plastic. The circuitry is typically of low mass, so it has inherently small magnetic properties.

The first embodiment of the system 50 (FIG. 2) is configured to only sends an alert signal to the control room; the alert devices in the magnet room have no microphone for allowing audio transmission. The system can be configured to send or generate, upon activation of an alert device, a pre-recorded message asking for help in a given MRI scanner room. In this example, the system includes alert devices 62A, 62B attached on both side of the magnet of the MRI system in the magnet room (MR), for convenient access by the technologist.

Figure 2:
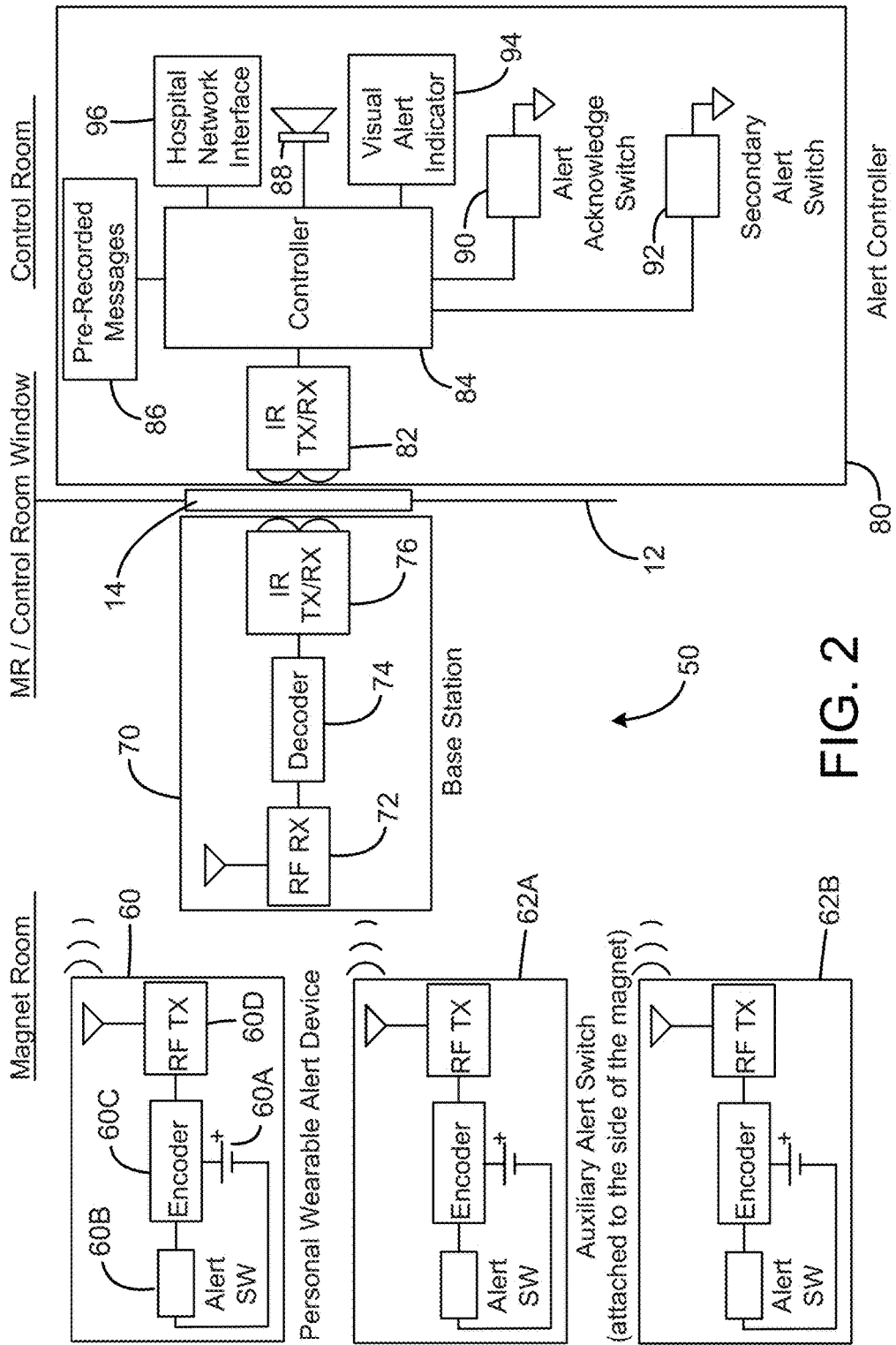
FIG. 2 is a schematic block diagram illustrating elements of a first exemplary embodiment of an MRI alert system in accordance with features of the invention.
Figure 4:
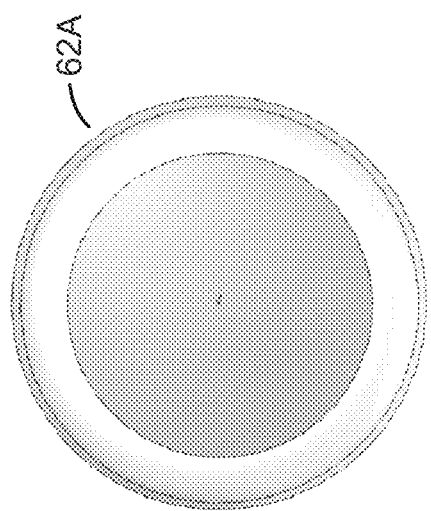
FIG. 4 is a front view of an exemplary embodiment of a stand-alone alert device configured for attachment to a structure in the MRI magnet room.
Figure 3:
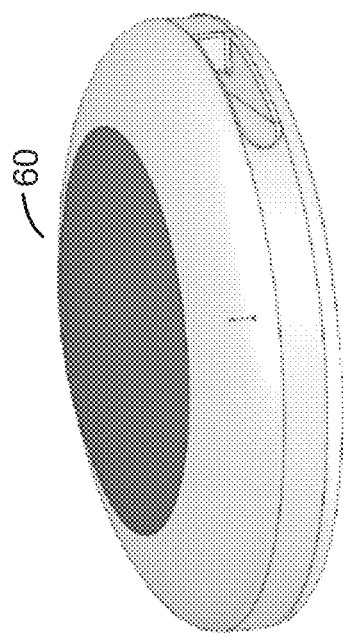
FIG. 3 is a diagrammatic isometric view of an exemplary embodiment of a wearable alert device.

Personal Wearable Alert Device (60):

This is a battery-operated device (60) provided to each technologist. FIG. 2 shows a schematic block diagram of the device, and FIGS. 1C, 1D, 1E and 3 show an exemplary embodiment. The device 60 includes a MRI-compatible battery 60A, an alert switch 60B, an encoder 60C and an RF transmitter 60D, similar to that used in a car remote control. Battery charge information may be transmitted to the base station on each transmission. In addition, there will typically be an indicator (e.g. an LED or other light source, or an audible generator) on the device itself that alerts the technologist of the low battery condition. The alert device includes an alert switch or button 60B, which is connected to an encoder module 60C, which produces, in this example, 4096 unique codes; each personal device will be assigned a unique code which is used for traceability of an alert incident. In this exemplary embodiment, the alert device 60 includes an RF transmitter 60D, which transmits a modulated signal to the base station, every time the alert switch is depressed.

Auxiliary Alert Devices (62):

The system 50 further includes auxiliary alert devices 62A, 62B, disposed on opposite sides of the MRI magnet (see FIG. 2). These devices provide additional security, and allow the patient in some instances to activate the system, and also provides additional locations at which a technologist or other care giver can activate an alert, even if not wearing a device 60. The auxiliary devices are similar in circuitry to the wearable alert device 60, but may optionally be connected to a source of power other than a battery, such as a transformer circuit.

Base Station (70):

The system includes a base station 70, disposed in the magnet room, adjacent the MR/control room window 12. The base station 70 receives the transmitted code from an alert device in the magnet room, decodes it, and transfers it via IR through the glass of the MR/Control room window 14 to the alert controller located in the control room. Thus, the base station includes an RF receiver (RF RX) 72, which receives and demodulates the transmitted code. A decoder 74 decodes the message and prepares it for transmission via IR transmitter 74 to the alert controller system in the control room. The IR transmitter 74 transmits serial messages in this exemplary embodiment. The emitter of the device 76 can be placed adjacent the window as generally indicated in FIG. 2. The base station may be powered by a non-magnetic battery for convenience, and will have a non-magnetic housing, e.g. plastic or aluminum. The base station is typically placed at a sufficient distance from the magnet that it will not have any significant impact on the MRI imaging.

The alert controller system 80 (FIG. 2) receives the alert message from the magnet room and alerts the technologist in the control room via audible and visual indications. The controller also plays pre-recorded messages during an alert. It also interfaces to the facilities network to alert further help and for event recording and time keeping.

As shown in the block diagram of FIG. 2, the alert controller system 80 includes an IR transmitter/receiver TX/RX 82, configured to transmit and receive serial messages. A controller 84 such as a PC or other computer manages network tasks and alert indications, and responses to the alert acknowledge and secondary alert switches 90, 92. Other implementations may utilize a microcomputer or microcontroller.

Alert messages in the native language are pre-recorded, and stored in a memory 86 for playback during an alert mode.

The alert control system 80 includes an alert acknowledge switch 90 in the control room. After an alert situation has been recognized by the technologist in the control room, by pressing this switch the alert system goes back to a normal state.

The alert control system 80 may also include a secondary alert switch 92 in the control room. In case of emergency while an MRI procedure is in session, by pressing this button, the technologist can alert nurses or medical staff for help. This is similar to a Code Blue in the hospital.

The alert control system may also include a visual alert indicator 94 in the control room. In one exemplary embodiment, this indicator may include different colored LEDs or an LCD display to visually alert other technologists in the control room.

The control room speaker 88 is connected to the controller, and plays an audible alert tone followed by the pre-recorded message and then repeats until the alert is acknowledged by actuating the alert acknowledge switch The alert control system may also include a network Interface 96, which may be a wired or wireless network interface, allowing the system 50 to send information via network to other parties within the MRI or other facility.

The system 80 and controller 84, in an exemplary embodiment, is programmed to perform the following steps:

(i) In a normal mode, monitor the transceiver 82 for incoming alert signals;

(ii) upon receipt of an alert signal from an alert device 60, 62A or 62B, enter an alert mode, and generate an audible alert signal and a pre-recorded audible alert message, and optionally a visible alert signal;

(iii) monitor the alert acknowledge and secondary alert switches in the control room;

(iv) after the alert acknowledge switch is activated, return the system to the normal mode;

(v) if the secondary alert switch is activated during an MRI signal procedure, generate an emergency alert to alert nurses and other medical personnel of an emergency situation;

(vi) upload information regarding the alert via a network to others.

Figure 5:
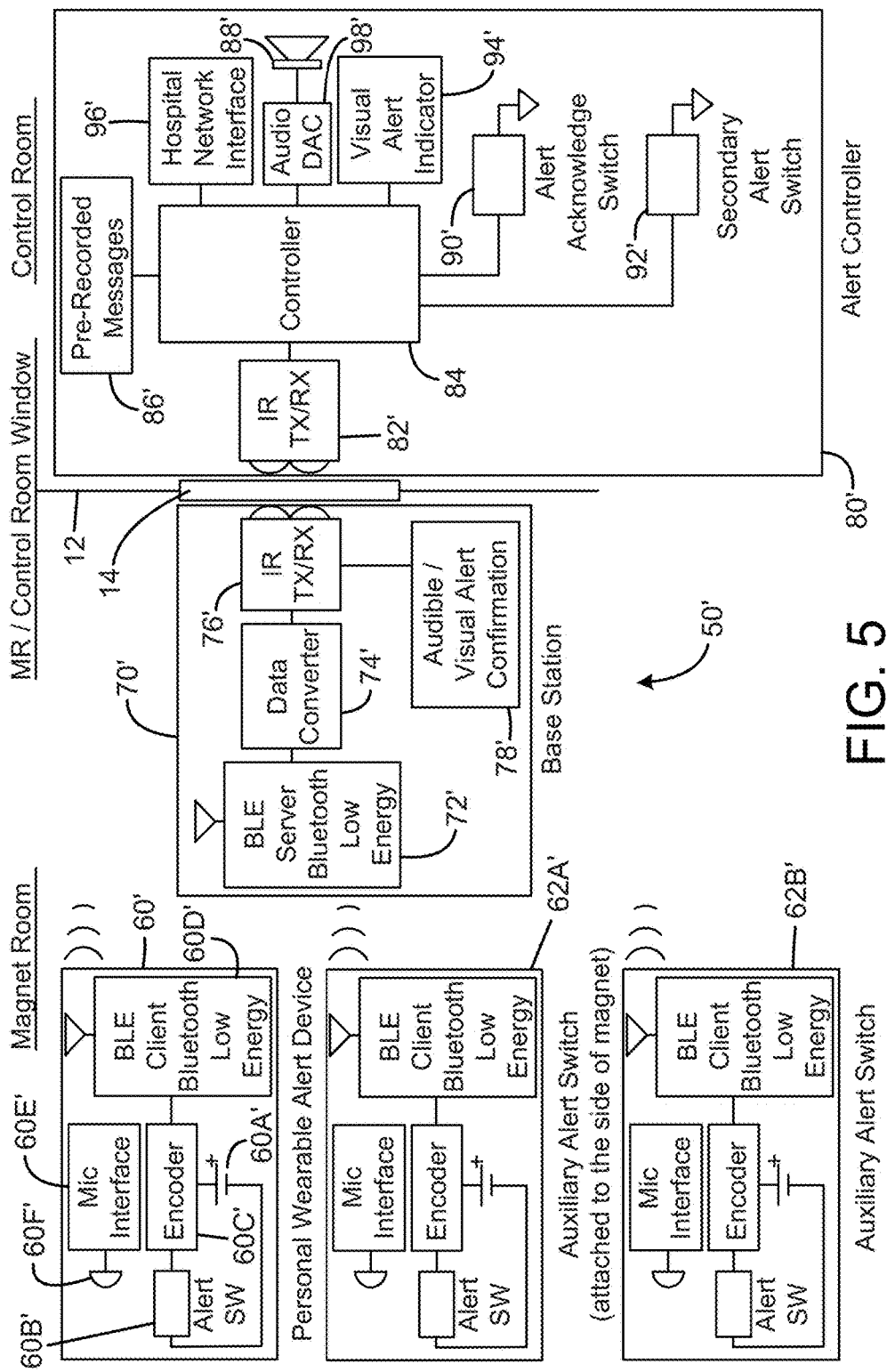
FIG. 5 is a schematic block diagram illustrating elements of a second exemplary embodiment of an MRI alert system.

Another exemplary embodiment of an alert system is illustrated in the schematic block diagram of FIG. 5. In one form, the system has the capability to send an alert signal and to transmit voice. The alert device has a built-in microphone and microphone interface, and uses Bluetooth/Low energy Bluetooth™ (BLE) for power saving, or similar technology to transmit the voice and the alert signal to the receiver module in the window of the MR/control room wall. The alert device includes a BLE client transmitter/receiver. The base station in the MR includes a BLE server which receives the wireless transmissions from the alert device. A data converter in the base station converts the signal to IR, and an IR transmitter receiver positioned adjacent the window transmits the IR signals through the window to the control room.

In a typical system, a Bluetooth device battery would last only few days before needing to be recharged. In addition, the typical device would need to be paired like a headphone or smart phone. With the new technology of Low Energy Bluetooth™ the battery can last months before charging and there is no need for pairing.

In this embodiment of the system, the technologist wearing the alert device 60' can actually talk while depressing the alert button. And, depending on the setting of the system, his or her voice and the alert signal can be heard in the control room/nurse station or any place the user chooses to direct it.

As with the first embodiment, the alert control system 80' in the control room includes an IR transmitter/receiver 82, and receives the IR signals from the magnet room. In the control room, the system responds to the alert signal as before with pre-recorded spoken messages, and the voice signals from the alert device in the magnet room are also played through the speaker 88'. The control system has a network interface 96', and the capability to be connected via a network address to any location such as a nurse station or radiology reception for help.

The system 50' of FIG. 5 includes a personal wearable alert device 60'. This battery-operated device provided to each technologist has an alert switch or button 60B' and a microphone 60F' with a microphone interface 60E'. It is intended to be used during the time that technologist requires additional help for patient management. Once the alert switch is depressed, an identification code uniquely identifying the alert device is transmitted and then the microphone is enabled and the technologist's voice is transmitted for 30 seconds or any other predefined time duration. There are visual indicators on the device for the microphone activation and battery status. This information is available at the alert control system as well.

The auxiliary alert devices 62A'. 62B' attached to the magnet may also have voice communication capability.

The alert device includes an encoder module 60C', which in this example produces 4096 unique codes; each personal alert device in the system will be assigned a unique code which is used for traceability of an alert incident. The alert device includes a BLE client 60D' which formats audio and ID messages into a BLE message standard and transmits it to the base station 78'.

The base station 78' may typically also be a battery powered device for ease of installation. The base station receives the transmitted code and microphone audio via BLE, and transfers it via IR through the glass of the MR/Control room window to the alert control system 80' located in the control room. Once the alert message has been confirmed by the alert controller, the base station provides audible and visual indications by module 78'. Thus, the base station, in this example, includes a BLE Server 72', which receives and transfers the alert code and microphone audio to be decoded to a data converter 74', which decodes the message/microphone audio and prepares it for transmission via IR to the alert control system. The base station IR transmitter/receiver 76' transmits and receives serial messages to and from the alert control system in the control room.

The alert control system 80' receives the alert message from the magnet room and alerts the technologist in the control room via audible (speaker 88') and visual indications (visual indicator 94'). It also plays pre-recorded messages during alert. it also interfaces to the facilities network to alert further help and for event recording and time keeping.

The control system 80' includes an IR transmitter/receiver 82', to transmit and receive serial messages. The system includes the controller 84' which manages network tasks and alert indications, responses to the alert acknowledge and secondary alert switches 90', 92'.

The pre-recorded messages are stored in digital memory 86', and include alert messages for playback during an alert mode.

The system 80' includes an alert acknowledge switch 94'; after an alert situation has been recognized by technologist by pressing this switch, the system goes back to the normal state.

The secondary alert switch and visual alert indicator perform functions as described above regarding the first embodiment.

An audio DAC/amplifier 98' converts the audio stream from either the pre-recorded message or the audio from the alert device to analog audio signals and drives the speaker. The speaker 88' generates an audible alert tone followed by the pre-recorded message and then repeats until the alert is acknowledged via the alert acknowledge switch 90'.

The network interface in a wired or wireless network interface 96', and allows the device to send information via network to other parties within the facility.

Although the foregoing has been a description and illustration of specific embodiments of the invention, various modifications and changes thereto can be made by persons skilled in the art without departing from the scope and spirit of the invention. For example, the IR link between the magnet room and the control room could be replaced with a Wi-Fi link, an electrical cable (passed through the patch panel with low pass or bandpass filtering), or by an optical fiber link. The optical fiber or electrical cable could run between the base station in the magnet room and the control room. Similarly, the base station could include a Wi-Fi transceiver which communicates with a Wi-Fi transceiver in the control room.

The invention claimed is:

1. An alert system for providing the capability for a care giver or technologist in a medical procedure room to send an alert signal concerning a patient undergoing the medical procedure to personnel in a control room outside the procedure room, the system comprising:
- an alert device carried by or available to the care giver or technologist in the procedure room, the device including an alert switch configured for manual activation by the care giver or technologist, and a wireless signal transmitter for generating encoded alert signals upon activation of the alert switch, and wherein the alert device is substantially non-magnetic;
- an alert control system in the control room, comprising a signal receiver, a memory for storing pre-recorded messages, an audio transducer and a controller, the controller responsive to alert signals generated by the alert device to generate alert signals including generating pre-recorded messages from the audio transducer.

2. The system of claim 1, wherein the procedure room is a magnet room of an MRI installation, and the alert device is is MRI-compatible so as not to affect MRI processing and magnetic fields of the MRI installation do not affect operation of the alert device.

3. The system of claim 2, further comprising a base station disposed in the procedure room, the base station comprising a receiver for receiving the encoded signal, a decoder or data converter responsive to the received signal, and a transmitter for sending the signals from the decoder or data converter to the receiver of the alert control system.

4. The system of claim 3, wherein the base station transmitter comprises an Infrared (IR) transmitter for transmitting an IR signal through a window separating the MRI magnet room from the control room, and the receiver of the alert control system comprises an IR receiver positioned to receive the IR signals from the IR transmitter.

5. The system of claim 3, wherein the base station transmitter is connected to the receiver of the alert control system by an optical fiber link.

6. The system of claim 3, wherein the base station transmitter is connected to the receiver of the alert control system by an electrical signal cable.

7. The system of claim 3, wherein the alert signal transmitter is an RF transmitter, and the base station receiver is an RF receiver.

8. The system of claim 3, wherein the alert signal transmitter is a Bluetooth™ transmitter, and the base station receiver is a Bluetooth™ server.

9. The system of claim 1, wherein the alert device is a wearable device configured to be worn by the care giver or technologist in the procedure room.

10. The system of claim 1, wherein the alert device includes a device mounted to a structure in the procedure room.

11. The system of claim 1, wherein the alert device further includes a microphone, and the alert device and the system are configured to provide one-way or two-way voice communication between the alert device and the control system.

12. The system of claim 1, wherein the control system further includes an alert acknowledgment switch in the control room for generating a signal to the controller to acknowledge the alert has been received and to put the system back to a normal mode.

13. The system of claim 1, wherein the control system further includes a network interface to communicate alert conditions to a facility network such as a hospital network.

14. The system of claim 13, wherein the control system further includes a secondary alert switch for generating an emergency condition alert signal.

15. An alert system for a care giver or technologist in a shielded MRI magnet room to send an alert signal regarding a patient undergoing an MRI procedure to personnel in a control room outside the magnet room, with a window between the magnet room and the control room, the system comprising:
- an alert device carried by or available to the care giver or technologist in the magnet room, the alert device including an alert switch configured for manual activation by the care giver or technologist, and a wireless signal transmitter for generating wireless alert signals upon activation of the alert switch by the caregiver or technologist;
- a base station disposed in the magnet room, the base station comprising a receiver for receiving the encoded signal, a decoder or data converter responsive to the received signal, and an Infrared (IR) transmitter for transmitting IR signals representative of the signals from the decoder or data converter;
- an alert control system in the control room, comprising a signal receiver positioned to receive the IR signals passed through the window from the base station, a memory for storing pre-recorded messages, an audio transducer and a controller, the control system responsive to IR alert signals emitted by the base station to generate alert signals including generating audible alert signals indicating that assistance is needed in the magnet room.

16. The system of claim 15, wherein the alert device is substantially non-magnetic, and powered by a non-magnetic battery so as not to affect MRI processing.

17. The system of claim 15, wherein the alert signal transmitter is an RF transmitter, and the base station receiver is an RF receiver.

18. The system of claim 15, wherein the alert signal transmitter is a Bluetooth™ transmitter, and the base station receiver is a Bluetooth™ server.

19. The system of claim 15, wherein the alert device is a wearable device configured to be worn by the care giver or technologist in the MRI magnet room.

20. The system of claim 15, wherein the alert device is configured as a stand-alone device mounted to the MRI magnet structure in the magnet room.

* * * * *